(12) United States Patent
Hogan

(10) Patent No.: US 11,344,195 B2
(45) Date of Patent: May 31, 2022

(54) METHOD AND SYSTEM FOR MONITORING CONTROL CAPABILITY

(71) Applicant: Joshua Noel Hogan, Los Altos, CA (US)

(72) Inventor: Joshua Noel Hogan, Los Altos, CA (US)

( * ) Notice: Subject to any disclaimer, the term of this patent is extended or adjusted under 35 U.S.C. 154(b) by 27 days.

(21) Appl. No.: 16/325,684

(22) PCT Filed: Oct. 15, 2018

(86) PCT No.: PCT/US2018/055958
§ 371 (c)(1),
(2) Date: Feb. 14, 2019

(87) PCT Pub. No.: WO2019/075485
PCT Pub. Date: Apr. 18, 2019

(65) Prior Publication Data
US 2020/0359889 A1    Nov. 19, 2020

Related U.S. Application Data

(60) Provisional application No. 62/572,539, filed on Oct. 15, 2017.

(51) Int. Cl.
*A61B 5/05* (2021.01)
*A61B 3/14* (2006.01)
*A61B 3/10* (2006.01)
*A61B 3/113* (2006.01)
*A61B 3/00* (2006.01)
*A61B 3/12* (2006.01)
*A61B 3/18* (2006.01)

(52) U.S. Cl.
CPC ............ *A61B 3/113* (2013.01); *A61B 3/0025* (2013.01); *A61B 3/102* (2013.01); *A61B 3/1005* (2013.01); *A61B 3/1225* (2013.01); *A61B 3/14* (2013.01); *A61B 3/18* (2013.01)

(58) Field of Classification Search
CPC ..... A61B 19/5244; A61B 6/032; A61B 3/103; A61B 3/14; A61B 3/152; A61B 3/113; A61B 3/1225; A61B 3/1015
USPC ......... 600/427, 425, 407; 351/200, 205–206, 351/208–210, 221, 246
See application file for complete search history.

(56) References Cited

U.S. PATENT DOCUMENTS

| | | | | |
|---|---|---|---|---|
| 2012/0150029 A1* | 6/2012 | Debuc | ........................ | G06T 7/12 600/425 |
| 2014/0049753 A1* | 2/2014 | Bajramovic | ............ | A61B 3/102 351/247 |
| 2016/0174835 A1* | 6/2016 | Hogan | ................. | A61B 3/0025 351/221 |

* cited by examiner

*Primary Examiner* — Dawayne Pinkney

(57) ABSTRACT

A method and system for providing motion analysis data useful in identifying, monitoring, or treating neurological conditions. The preferred embodiment uses an optical coherence tomography system to obtain information about capability of motion control and control of involuntary eye movement. Alternate embodiments are taught.

5 Claims, 8 Drawing Sheets

Example image of 128 successive A-scans at substantially the same location of the retina showing two key layers, the ILM (inner limiting membrane) and the RPE (retinal pigment epithelium) and intermediate weaker layers.

Example image of 128 successive A-scans at substantially the same location of the retina showing greater variation in the axial alignment of the two key layers, the ILM (inner limiting membrane) and the RPE (retinal pigment epithelium)

Example plot of measured distance between the ILM and RPE for a total of approximately 1200 A-scans, depicted in the order in which they were acquired. The Y-axis shows the ILM to RPE distance in microns.

Example plot of measured distance between the ILM and RPE for a total of approximately 1200 A-scans, depicted in the order of increasing distance. The Y-axis shows the ILM to RPE distance in microns.

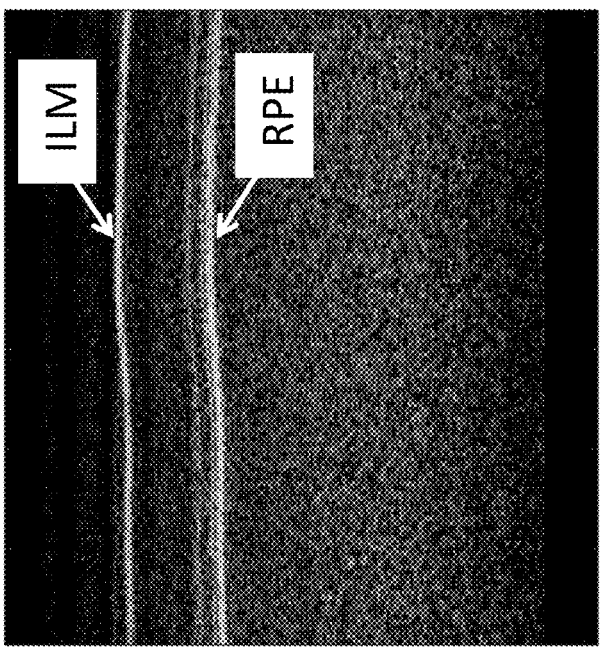
Fig. 7A
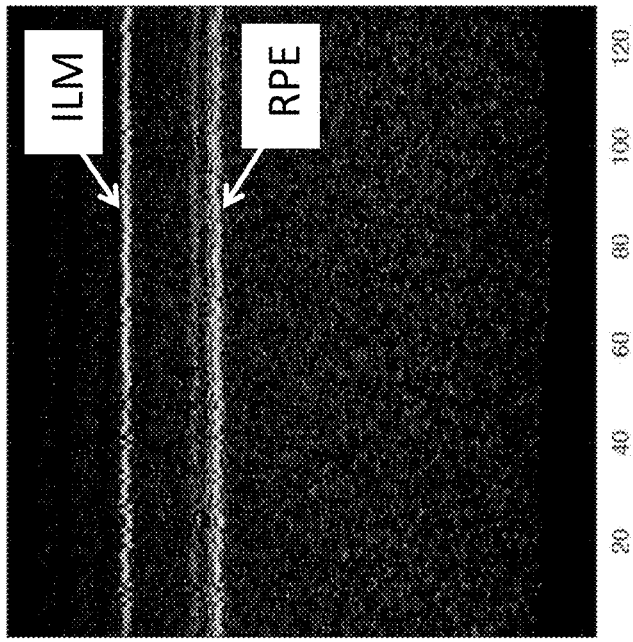
Fig. 7B
Fig. 7A is an example image of 128 successive A-scans at substantially the same location of the retina showing variation in the axial alignment of the ILM and RPE. Fig. 7B shows the same A-scans processed to axially align the RPE depth location.
Fig. 7

METHOD AND SYSTEM FOR MONITORING CONTROL CAPABILITY

FIELD OF USE

Optical coherent tomography of the eye and, more specifically, as eye data relates to neurologic conditions.

BACKGROUND

Motion, including eye motion, has been linked to neurological conditions. Evidence has linked certain motor based performance and characteristics of performance to neurologic conditions such as, Parkinson's, Multiple Sclerosis, and Alzheimer's.

Continued advances in medicine are providing drug therapies to alleviate conditions such as, Parkinson's, Multiple Sclerosis, and Alzheimer's.

For example, the drug Nilotinib (also referred to by the brand name Tasigna), has the potential of being a new treatment for Parkinson's disease by eliminating toxic proteins from the brain. Studies indicate that the daily use of nilotinib appears to in/prove symptoms of Parkinson's disease without causing serious adverse reactions.

Regularly monitoring the condition of the disease, in conjunction with the daily use of such a drug, would provide valuable information on the efficacy of the drug, could assist in more accurately titrating the drug, and could provide warning of an unexpected change in the onset or progression of the disease.

There is ongoing research involving examination of the retina in order to provide information pertinent to neurologic conditions, including, but not limited to Parkinson's, Alzheimer's, and Multiple Sclerosis.

Current methods of retinal examination typically involve using clinical scale optical analysis systems, such as clinical scale optical coherence tomography (OCT) systems, and detailed examination of components of the retina, such as retinal layers. Such detailed examination is typically performed by skilled professional researchers who possess considerable knowledge of the retina.

The requirement for clinical scale OCT system and for skilled professional researchers to interpret results make current methods impractical for routine monitoring for the onset or progression of neurologic conditions, such as, Parkinson's, Multiple Sclerosis, and Alzheimer's.

A low cost consumer level OCT system is under development for a home monitor of the onset or progression of age related macular degeneration (AMD) and diabetic retinopathy (DR). Aspects of this monitor are described in U.S. patent application Ser. No. 14/910,442 (U.S. Pat. No. 9,888, 841, titled, Head-mounted Optical Coherence Tomography). The approach consists of making a measurement of the retinal thickness at or close to the center of the fovea.

Aspects of an AMD monitor are also described in patent application PCT/US18/25748, titled Home Monitoring Optical Coherence Tomography System.

Patent application Ser. No. 14/910,442, and U.S. Pat. No. 9,888,841, and patent application PCT/US18/25748 are all three incorporated by reference herein as if fully set down.

While the device described in patent application Ser. No. 14/910,442 can be low cost and suitable for home monitoring, it is not anticipated to provide the detailed high resolution volumetric imagery likely required for successful monitoring for neurologic conditions, such as, Multiple Sclerosis, Parkinson's, and Alzheimer's.

A recent US patent, U.S. Pat. No. 9,412,161, taught movement, including video of eye movement as pertaining to neurologic conditions, namely, Parkinson's, Alzheimer's, and Multiple Sclerosis. However, the system depends on cameras and video of largely conventional types. Moreover, the motion detected, particularly with respect to the eye, is limited to outward manifestations of movement, e.g. gaze nystagmus. Furthermore, with the approach disclosed in U.S. Pat. No. 9,412,161, the resolution with which motion is detected is of the order a millimeter (as little as 0.5 to 5 mm).

There is therefore an unmet need for low cost, consumer level system and method of examination that provides data pertinent to neurological conditions, including but not limited to Parkinson's, Multiple Sclerosis, and Alzheimer's and one that is suitable for doing so on a routine basis, ideally as a home monitor.

BRIEF SUMMARY OF THE INVENTION

The invention provides a method and system for providing motion analysis data useful in identifying, monitoring, or treating neurological conditions. The preferred embodiment uses an optical coherence tomography (OCT) system to obtain information about a subject's capability of motion control and control of eye movement. In one embodiment the accuracy with which a subject can fixate on an optical beam or other fixation light or image is determined. In another embodiment, data related to the automatic alignment of the OCT system is analyzed to provide a measurement of the motion control capability of the subject.

In the preferred embodiment, the OCT system provides central macular thickness data, said data obtained as subject is performing controlled eye motion by fixating on a visible light beam or displayed image. In the preferred embodiment the visible fixation light beam is the OCT probe beam. In another embodiment the visible fixation light beam has a wavelength significantly different from the wavelength of the OCT probe beam. In another embodiment the fixation is by means of observing aspects of a displayed image.

In one embodiment the wavelength of the OCT probe beam is centered approximately about 805 nm (perceived as the color red) and the wavelength of the fixation light beam is approximately 512 nm (perceived as the color green).

In the preferred embodiment, the subject fixates on the OCT probe beam, thereby causing the probe beam to be approximately centered on the center of the fovea of the retina. The OCT system is automatically aligned in depth such that the OCT gating range (the range where the OCT system can make interferometric measurements) is centered (in depth) on the retina.

The OCT system is triggered to take retinal depth scans that each include the highly reflecting and deeper retinal pigment epithelium (RPE) and the weakly scattering front surface of the retina, the inner limiting membrane (ILM). These scans are processed to determine a measurement of the distance between the RPE and the ILM that is referred to as the central macular thickness (CMT).

Due to inevitable natural motion of the subject, the acquired scans dither about the center of the fovea. This produces scans that yield a distribution of the measured value of the CMT. The statistical distribution of these measurements is a function of how well the subject can fixate, which in turn is a function of the motion control capability of the subject. Therefore analyzing the statistical distribution of such measurements over time, i.e. on a daily, weekly or monthly basis, provides a mechanism for monitoring the motion control capability of the subject.

In an alternate embodiment, the OCT system provides a plurality of B scans along with an indicator of scan quality expressed as signal to noise ratio, wherein value of or change in signal to noise ratio provides eye movement control data which can be used to monitor the motion control capability of a subject and thereby the onset or progression of a disease condition that affects the ability to control motion.

In an alternate embodiment, one or more of the dynamic feedback control signals of the OCT system are analyzed to obtain information regarding the motion control capability of the subject. As described above, the OCT system is automatically aligned in depth such that the OCT gating range (the range where the OCT system can make interferometric measurements) is centered (in depth) on the retina. This is accomplished by detecting the distinctive strong interference signal from the RPE and locking on to this signal by automatically repositioning the OCT system in depth and also automatically adjusting the optical length of the reference arm of the OCT system to maintain correct depth alignment of the OCT system with respect to the retina.

The frequency content of the feedback signals that accomplish this automatic alignment is affected by the subject's ability to control motion. A subject with good motion control is able to maintain a more stable position with respect to the OCT system and therefore require lower compensation effort (and hence a lower frequency content) from the automatic alignment system.

As a subject's ability to control motion changes over time the frequency content of the required feedback signal will also change to reflect the loss or gain in motion control. Analyzing and monitoring statistical aspects of the automatic control feedback signals therefore provides a measurement of the subject's motion control capability.

Similarly other feedback signal for automatic control or alignment can be used to monitor a subject's motion control capability. For example, automatic lateral alignment of the OCT system to the subject's eye may also involve feedback signals whose frequency content can be monitored as a measure of the subject's motion control capability.

In general the feedback signal for automatic control or alignment of any device that is affected by a subject's ability to control their movement can be analyzed to monitor a subject's motion control capability and thereby used to monitor the onset or progression of a disease condition that affects the ability to control movement or motion.

In a further embodiment, the system provides any or all of the data recited hereinabove. In some embodiments, the OCT system is a multiple reference OCT system. In other embodiments the OCT system is a conventional time domain OCT system, a Fourier domain OCT system, either swept source or spectral domain, or a mode-locked OCT system.

The inventive system, comprised of an optical coherent tomography system, including a data processor, memory, and output of data to human perceptible form.

The system and method taught herein provide data pertinent to one or more neurological conditions. Pertinent is intended to mean: bearing on predictive assessment, pertaining to risk factors, monitoring at least one known condition, monitoring at least one drug protocol, or bearing on assessment of a factor having a direct or indirect relationship to neurologic condition.

Alternate embodiments of the invention include analysis of motion compensation data to provide indicators pertaining to degree of control over movement. This is especially useful in measuring subtle changes in degree of control of movement.

BRIEF DESCRIPTION OF THE DRAWINGS

The drawing are intended as an aid to understanding the invention:

FIG. 7A is an example image of 128 successive A-scans at substantially the same location of the retina showing variation in the axial alignment of the ILM and RPE.

FIG. 7B shows the same A-scans (of FIG. 7A) processed to axially align the RPE depth location.

DETAILED DESCRIPTION OF A PREFERRED EMBODIMENT OF THE INVENTION

The invention provides method and system for providing motion analysis data useful in identifying, monitoring, or treating neurological conditions. The preferred embodiment uses an optical coherence tomography (OCT) system to obtain information about a subject's capability of motion control and control of eye movement. In one embodiment the accuracy with which a subject can fixate on an optical beam or other fixation light or image is determined. In another embodiment, data related to the automatic alignment of the OCT system is analyzed to provide a measurement of the motion control capability of the subject.

In the preferred embodiment, the OCT system provides central macular thickness data, said data obtained as subject is performing controlled eye motion by fixating on a visible light beam or displayed image. In the preferred embodiment the visible fixation light beam is the OCT probe beam. In another embodiment the visible fixation light beam has a wavelength significantly different from the wavelength of the OCT probe beam. In another embodiment the fixation is by means of observing aspects of a displayed image.

In one embodiment the wavelength of the OCT probe beam is centered approximately about 805 nm (perceived as the color red) and the wavelength of the fixation light beam is approximately 512 nm (perceived as the color green).

In the preferred embodiment, the subject fixates on the OCT probe beam, thereby causing the probe beam to be approximately centered on the center of the fovea of the retina. The OCT system is automatically aligned in depth such that the OCT gating range (the range where the OCT system can make interferometric measurements) is centered (in depth) on the retina.

The OCT system is triggered to take retinal depth scans that each include the highly reflecting and deeper retinal pigment epithelium (RPE) and the weakly scattering front surface of the retina, the inner limiting membrane (ILM). These scans are processed to determine a measurement of the distance between the RPE and the ILM that is referred to as the central macular thickness (CMT).

Figure 1:
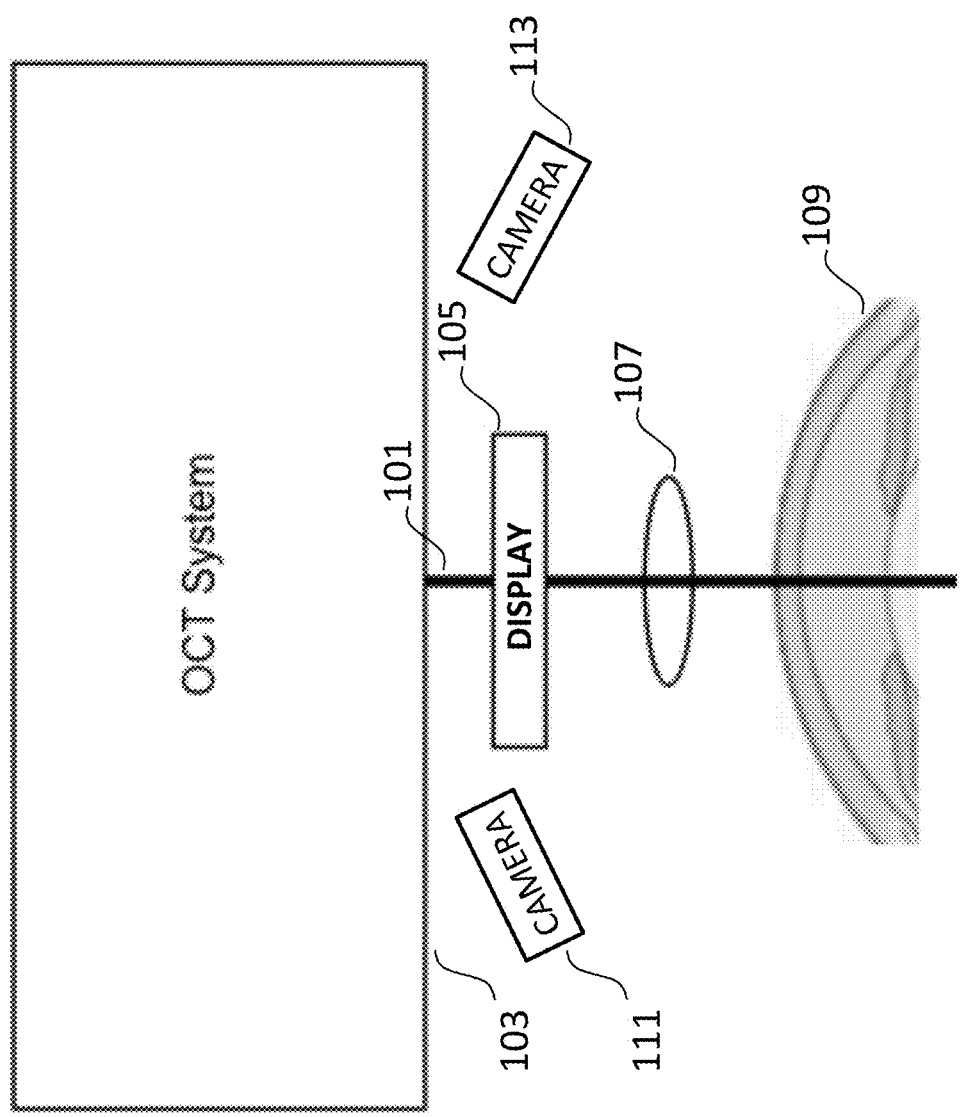
FIG. 1 schematically depicts a system according to the invention.

The preferred embodiment is illustrated in FIG. 1 where an optical probe beam 101 is output from an OCT system 103 and passes through an optional fixation display 105 and an optional refractive error correction lens 107 or lens combination and directed into the eye 109 whose retinal characteristics are to be measured.

The OCT beam is aligned in lateral directions to maintain the probe beam centered on the pupil of the eye typical by using simple motors and positional information from one or two cameras 111 and 113.

The OCT gate of the OCT system is also depth aligned with respect to the retina such that the interference signals from the ILM and RPE are within the OCT depth scan range. That is, the ILM and RPE are within an OCT depth scan, also referred to as an A-scan. This depth alignment is typically maintained by either adjusting, by means of a motor, the path length of the OCT reference path in response to inevitable movement of the eye being measured, or, in the case of a miniature OCT system, by moving the OCT system in the depth direction by means of a motor.

The depth information to maintain the OCT gate appropriately centered is derived from the interference signals from the ILM and RPE.

Figure 2:
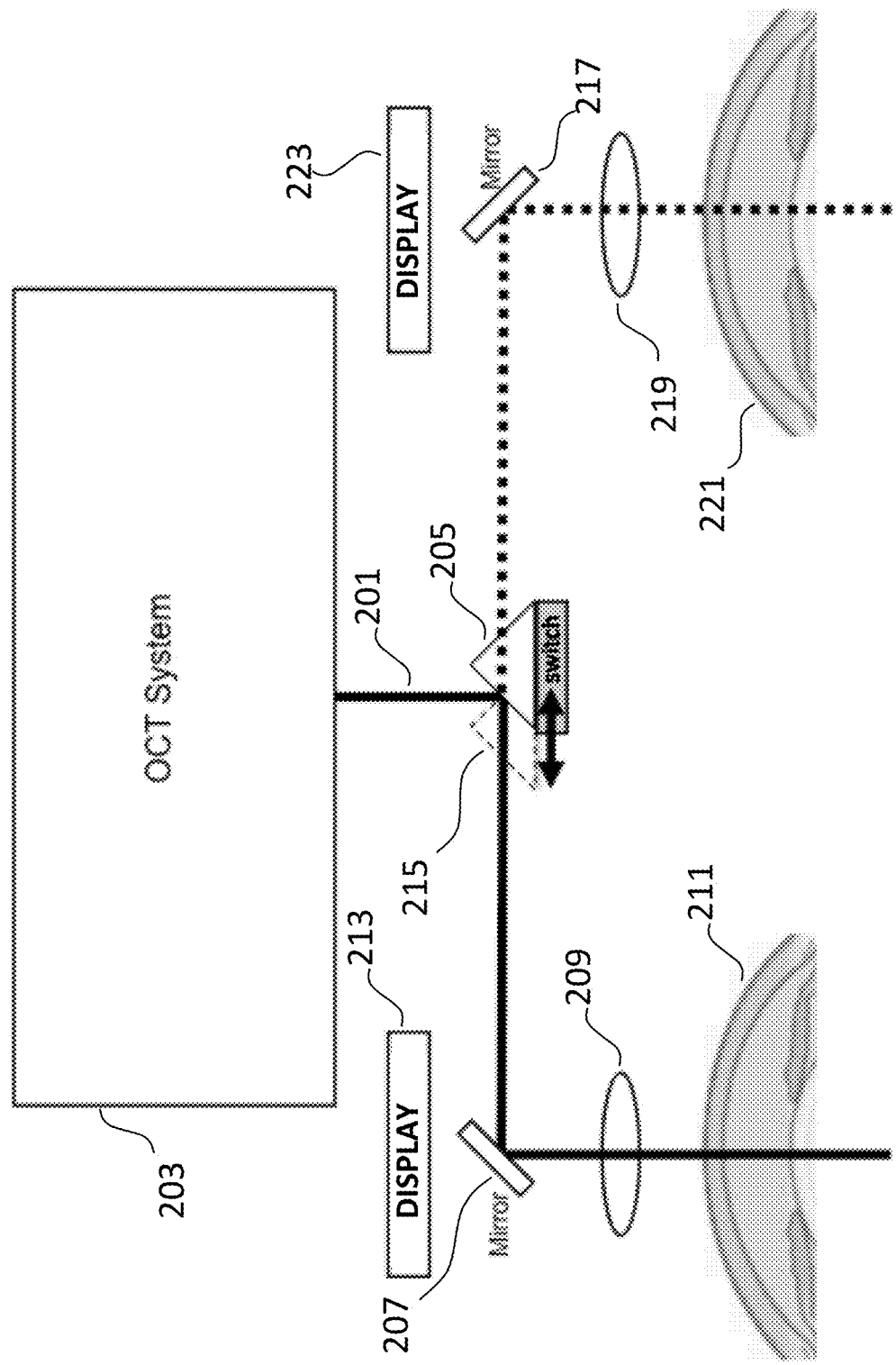
FIG. 2 schematically depicts an alternate embodiment of a system according to the invention.

An alternative embodiment, suitable for making measurements on both eyes is depicted in FIG. 2 where the probe beam 201 of the OCT system 203 is directed via a switchable two sided mirror 205 to a turning mirror 207, through an optional refractive error correcting lens or lens combination 209, into the eye 212 to be measured. As with the preferred embodiment, fixation is achieved either by fixating on the probe beam or on an aspect of the optional display 213.

As also with the preferred embodiment, lateral and depth alignment is maintained on the retina of the eye 211 to be measured by lateral motors and reference path length adjustment (or depth movement of the OCT system) using cameras (not shown) and the interference signals from the ILM and RPE.

The system of FIG. 2 can measure aspects of the second eye 221 by switching the moveable two sided mirror 205 to a second position indicated by the dashed triangle 215 to direct the probe beam to a second mirror 217 which directs the probe beam through a second optional lens or lens combination 219, into the second eye 221 to be measured.

Fixation is achieved either by fixating on the probe beam or on an aspect of the second optional display 223. Fixation may also be achieved by using the fellow, or contra-lateral eye to fixate on the display associated with the eye not being measured.

Figure 3:
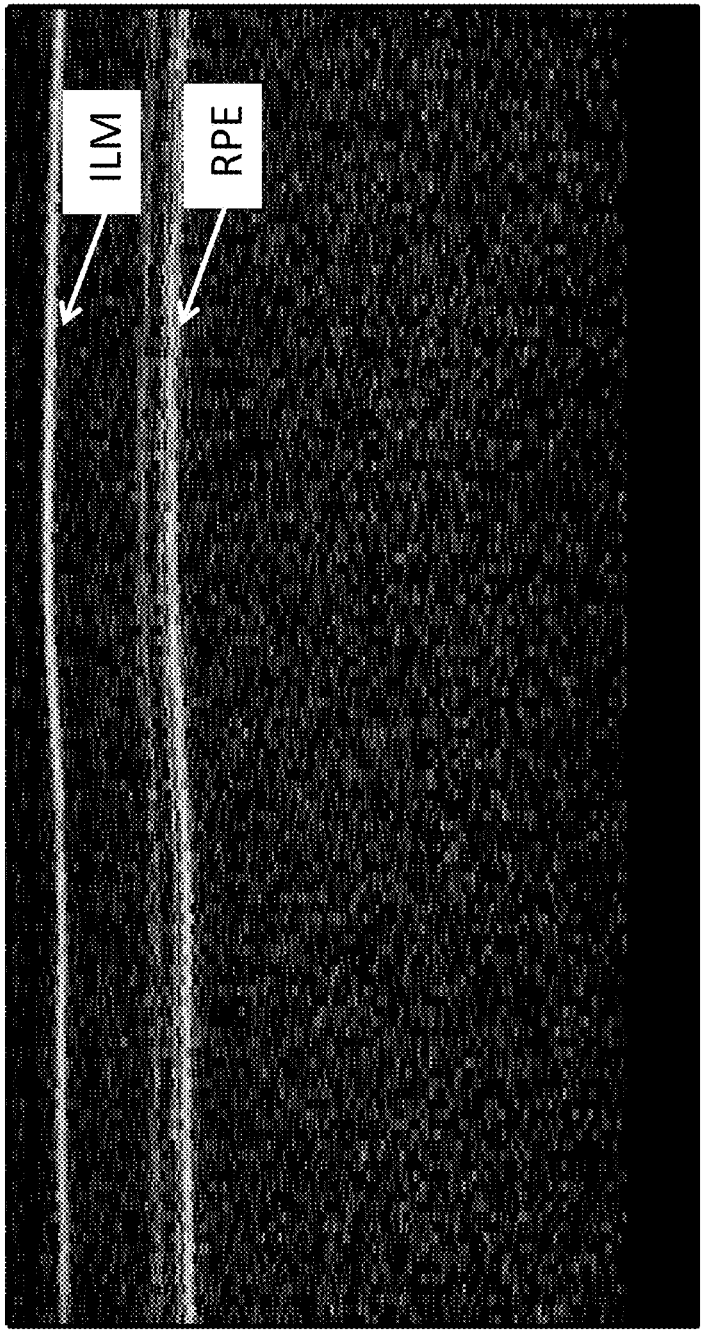
FIG. 3 shows an image of 128 successive A scans at substantially same location of the retina showing ILM (inner limiting membrane) and RPE (retinal pigment epithelium)

FIG. 3 is an example image of 128 successive A-scans at substantially the same lateral location of the retina showing two key layers, the ILM (inner limiting membrane) and the RPE (retinal pigment epithelium) and intermediate weaker layers.

Figure 4:
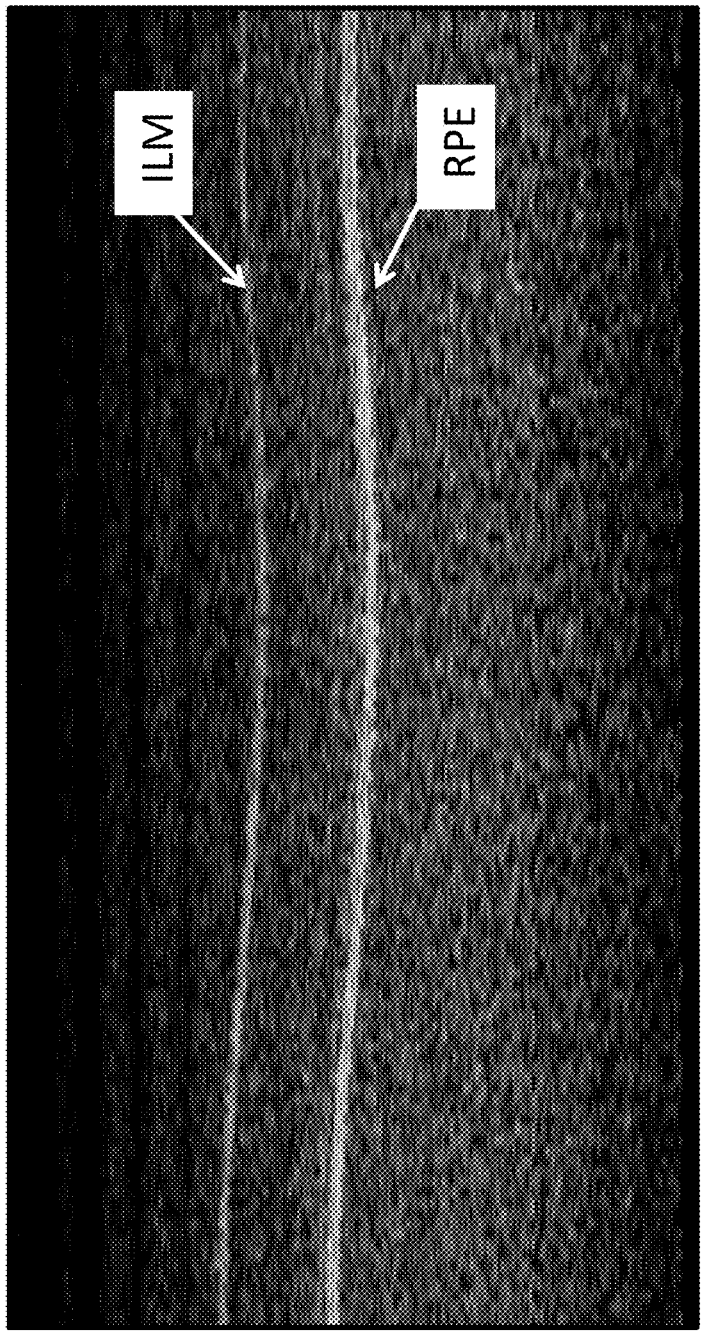
FIG. 4 shows an image of 128 successive A scans at substantially same location of the retina showing greater variation in the axial alignment of the two key layers, ILM (inner limiting membrane) and RPE (retinal pigment epithelium)

FIG. 4 is another example image of 128 successive A-scans at substantially the same lateral location of the retina showing two key layers, the ILM (inner limiting membrane) and the RPE (retinal pigment epithelium). This set of A-scans shows more variation in the depth location of the ILM and RPE. However, the distance between the ILM and RPE remains substantially constant.

While in embodiments where the OCT system is being used to measure the distance between the ILM and RPE at center of the fovea, such measurements may be done at locations on the retina other than at or near the center of the fovea.

The frequency content of the signals that maintain the probe beam centered in the pupil and the OCT gate centered on the ILM and RPE provide information related to the ability of the individual whose eye is being measured to control motion. The frequency content of one or more of these signals thereby provides critical information about their ability to control motion. Monitoring the frequency content provides a mechanism for monitoring the motion control capability of the subject.

In one embodiment, one or more of the dynamic feedback control signals of the OCT system are analyzed to obtain information regarding the motion control capability of the subject. A measure of the motion control capability of the subject under test, is output in a visible form. This output may occur locally or may be transmitted to be output remotely, or may be stored for future use either locally or remotely.

Furthermore when a subject is fixating, either on the OCT probe beam or an aspect of a fixation display, due to inevitable natural motion of the subject, the acquired scans dither about the center of the fovea. This produces scans that yield a distribution of the measured value of the CMT (i.e. distance between the ILM and RPE).

Figure 5:
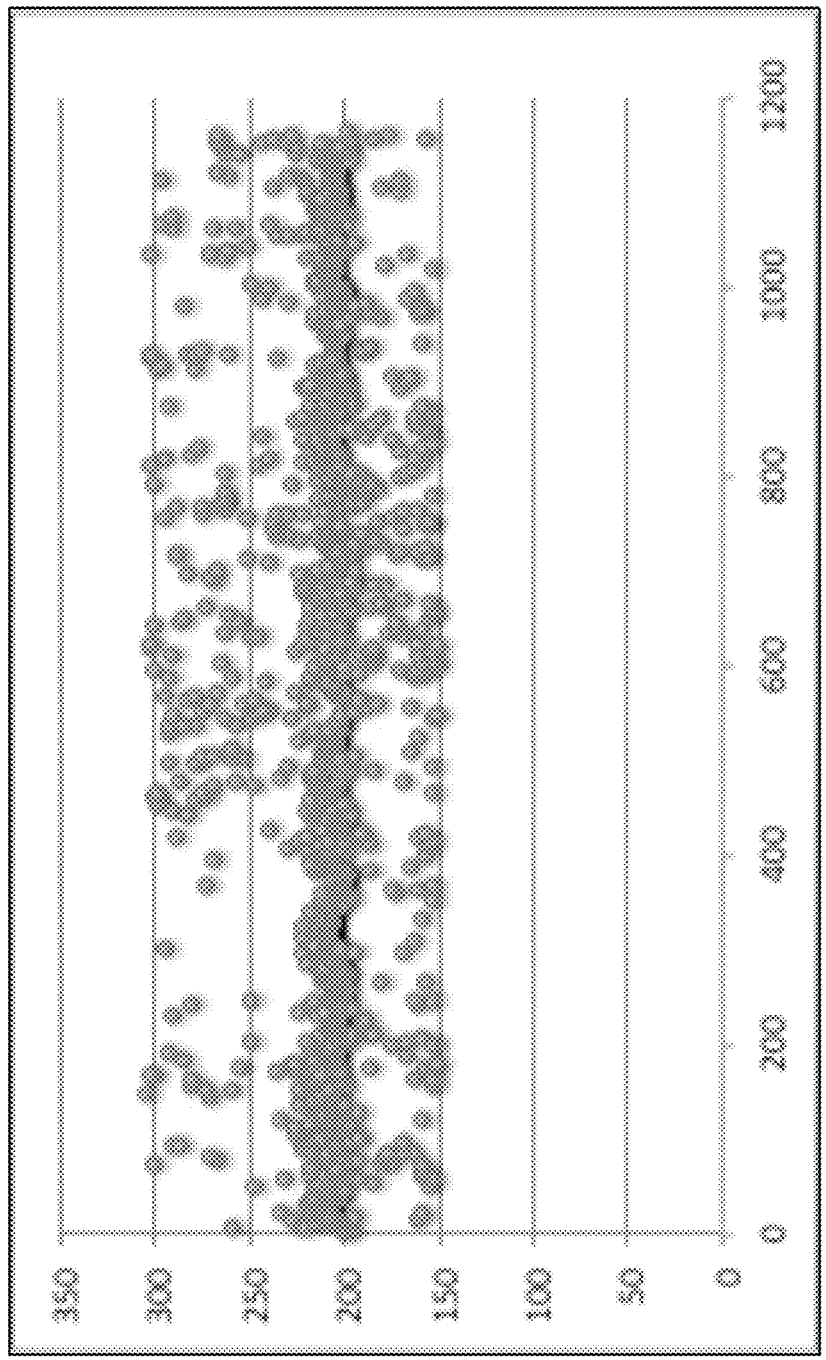
FIG. 5 shows a plot of measured distance between the ILM and RPE for a total of approximately 1200 A-scans, depicted in the order in which they were acquired. The Y-axis shows the ILM to RPE distance in microns.

An example of such a distribution of such measurements of the distance between the ILM and RPE for a total of approximately 1200 A-scans is shown in FIG. 5 Sheet 5 where the measurement results are depicted in the sequence (along the x-axis) in which they were taken. The y-axis shows the actual measured value of the ILM to RPE distance of this particular retina in microns.

Figure 6:
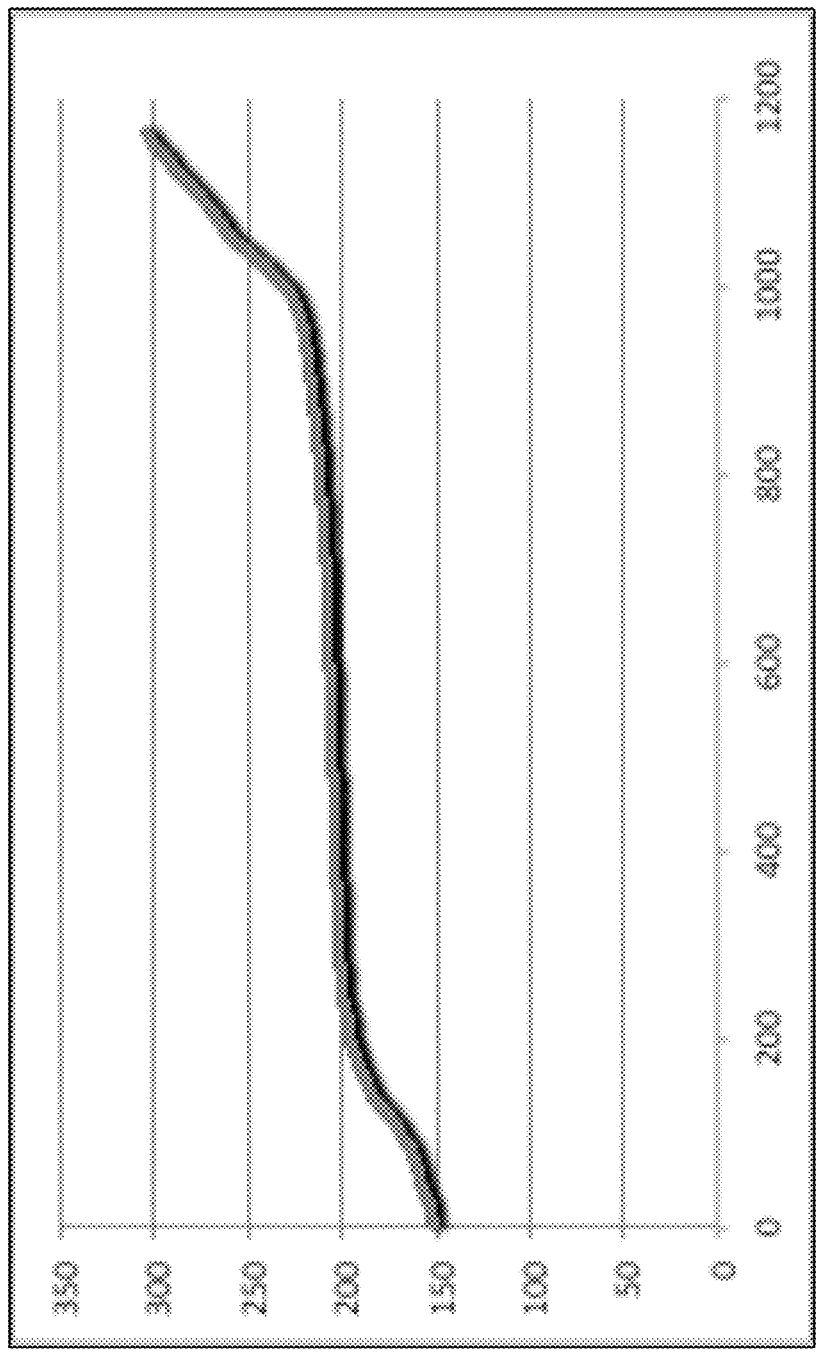
FIG. 6 shows a plot of measured distance between the ILM and RPE for a total of approximately 1200 A-scans, depicted in the order of increasing distance. The Y-axis shows the ILM to RPE distance in microns.

In FIG. 6 of Sheet 6, the same results are re-plotted, and here depicted in order of increasing value (along the x-axis). The average value of 210 microns provides a reliable measurement accurately related to the CMT.

The statistical distribution of these measurements is a function of how well the subject can fixate, which in turn is a function of the motion control capability of the subject. Therefore analyzing the statistical distribution of such measurements over time, i.e. on a daily, weekly or monthly basis, provides an additional or alternative mechanism for monitoring the motion control capability of the subject.

FIG. 7A Sheet 7 depicts an image of 128 successive A-scans at substantially the same location of the retina showing variation in the axial alignment of the ILM and RPE, while FIG. 7B of sheet 7 shows the same A-scans processed to axially align the RPE depth location. The aligned are then further processed to obtain, for example, an average value of the ILM and RPE distance, or the statistical variation of the ILM and RPE distance.

In an alternate embodiment, the OCT system provides a plurality of B scans along with an indicator of scan quality expressed as signal to noise ratio, wherein value of or change in signal to noise ratio provides eye movement control data which can be used to monitor the motion control capability of a subject and thereby the onset or progression of a disease condition that affects the ability to control motion.

As described above, the OCT system is automatically aligned in depth such that the OCT gating range (the range where the OCT system can make interferometric measurements) is centered (in depth) on the retina. This is accomplished by detecting the distinctive strong interference signal from the RPE and locking on to this signal by automatically repositioning the OCT system in depth and also automatically adjusting the optical length of the reference arm of the OCT system to maintain correct depth alignment of the OCT system with respect to the retina.

The frequency content of the feedback signals that accomplish this automatic alignment is affected by the subject's ability to control motion. A subject with good motion control is able to maintain a more stable position with respect to the OCT system and therefore require lower compensation effort (and hence a lower frequency content) from the automatic alignment system.

As a subject's ability to control motion changes over time the frequency content of the required feedback signal will also change to reflect the loss or gain in motion control. Analyzing and monitoring statistical aspects of the automatic control feedback signals therefore provides a measurement of the subject's motion control capability.

Similarly other feedback signal for automatic control or alignment can be used to monitor a subject's motion control capability. For example, automatic lateral alignment of the OCT system to the subject's eye may also involve feedback signals whose frequency content can be monitored as a measure of the subject's motion control capability.

In general the feedback signal for automatic control or alignment of any device that is affected by a subject's ability to control their movement can be analyzed to monitor a subject's motion control capability and thereby used to monitor the onset or progression of a disease condition that affects the ability to control movement or motion.

In a further embodiment, the system provides any or all of the data recited hereinabove.

In some embodiments, the OCT system is a multiple reference OCT system. In other embodiments the OCT system is a conventional time domain OCT system, a Fourier domain OCT system, either swept source or spectral domain, or a mode-locked OCT system.

The inventive system, comprised of an optical coherent tomography system, including a data processor, memory, and output of data to human perceptible form.

In one embodiment, two photonic modules are attached to a frame that fits on a subject's head in a manner that may be similar to a pair of spectacles. The frame is selected such that, when it is attached to the frame, the photonic module is at least coarsely aligned with at least one of the subject's eyes and such that the OCT scanning region is at least coarsely aligned with the retina of the eye, i.e. is aligned with the axial length of the eye.

Figure 8:
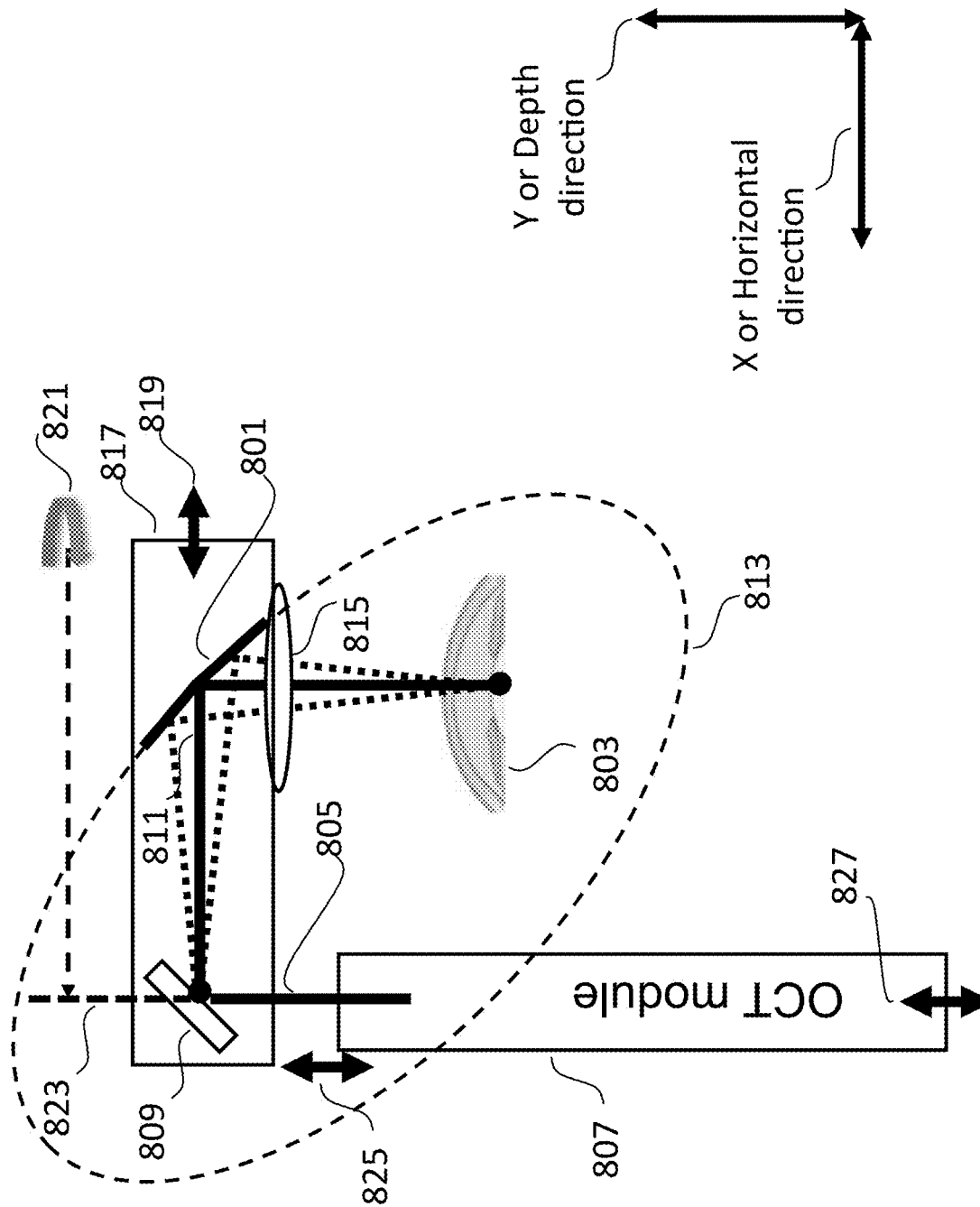
FIG. 8 depicts an alternate embodiment of a system according to the invention.

Key aspects of this preferred embodiment are depicted in and described with respect to FIG. 8 of Sheet 8. This embodiment includes a turning mirror 801 that directs the OCT beam into the Subject's eye 803. The collimated output beam 805 of an OCT module 807 is directed at the center of rotation of a 1 or 2 dimensional angular scanning device 809 (such as: a Galvo or Galvanometer scanner; an electromechanical actuator; or a MEMS device).

The beam 805 is redirected by the angularly scanning device 809 to the turning mirror 801 where it is again redirected by the turning mirror 801 to the pupil of the eye 803. The solid line 811 depicts the beam at one orientation of the angular scanning device 809, while the dashed lines on either side depict the beam at other orientations of the angular scanning device 809.

The geometry of the turning mirror 801 approximates to a two dimensional segment of an ellipsoid, one of whose foci is located at the center of rotation of the angular scanning device 809 while the other focus coincides with the location of the center of the pupil of the eye 803. An ellipse, with a circular dot at each focus is depicted as the dashed line 813.

One advantage of this ellipsoid based design is that the angularly scanning optical beam remains substantially centered on the center of the pupil of the eye 803, thereby enabling the beam to enter the eye 803 and to scan the retina. That is to say the angularly scanning optical beam pivots about a point in the eye substantially located at the center of the pupil of the eye, thereby optimizing the amount of light entering and leaving the eye and thereby scanning the retina.

Another advantage of this ellipsoid based design is that the length of the scanning optical beam remains substantially constant, thereby ensuring that the OCT path length remains substantially constant, thus avoiding the requirement of high speed axial length adjustment.

A further advantage is that a specific ellipsoid is selected for individual subjects so that the magnitude of the distance between the center of rotation of the angular scanning device 809 and the turning mirror 801 as well as the distance between the turning mirror 801 and the center of the pupil of the eye 803 can be optimized for individual subjects.

In some embodiments the ellipsoid based mirror is replaced by a spherical mirror whose surface closely approximates to the surface of an ellipsoid. The specific geometry of the turning mirror 801 is thus customized (or dispensed) for each individual subject.

An optional lens (or lens combination) 815 can be included to compensate for a subject's refractive error. The optional lens 815 is also a customized or dispensed component to correctly focus the optical beam on the retina. The optional lens 815 is depicted as a convex lens, however refractive error correcting lenses may be concave if appropriate. Refractive error correcting lenses may also be selected to account for the focusing effect of the turning mirror 801

In some embodiments the optional lens 815 is replaced by a pair of lenses, one of which acts as a condensing lens.

In some embodiments the diameter of the OCT probe beam 805 is sufficiently small so as not to require a refractive error correcting lens.

The angularly scanning or pivoting optical beam is centered on the appropriate location within the eye by the following motorized adjustments.

(a) translating the scanning module 817 and the OCT module 807 (as a rigid unit) in the horizontal (or X) direction as indicated by the double arrow 819.

(b) Vertical alignment (out of the plane of the drawing) is achieved by pivoting the scanning module 807 about the optical axis of the optical beam emerging from the OCT module 807, as indicated by the angular arrow 821 and the dashed line 823.

(c) The depth of the pivot point of the angularly scanning optical beam is optimized by translating the scanning module 817 and the OCT module 807 (as a rigid unit) in the depth (or Y) direction as indicated by the double arrow 825.

(d) In some embodiments, the OCT module 807 can also be adjusted with respect to the scanning module 817 in the depth direction as indicated by the double arrow 827 to align the OCT interference signals with respect to the retina of the eye.

(e) In some embodiments this adjustment is a fixed coarse alignment that is customized (or dispensed) for an individual subject with an additional fine adjustment for axial length alignment in the reference beam path of the OCT module.

The frequency content of the signals controlling any of the aspects in (a), (b), (c), (d) and (e) above may be processed to monitor the subject's motion control capability.

The system and method taught herein provide data pertinent to one or more neurological conditions. Pertinent is intended to mean: bearing on predictive assessment, pertaining to risk factors, monitoring at least one known condition, monitoring at least one drug protocol, or bearing on assessment of a factor having a direct or indirect relationship to neurologic condition.

While the invention is described with respect to a system that monitors the onset or progression of AMD (age related macular degeneration) by measuring the CMT thickness, or the distance between the ILM and RPE, the invention is applicable to OCT systems making retinal measurements other than CMT thickness, or OCT systems making measurements on the eye in areas other than the retinal area, such as axial length eye measurements, or measurements in the anterior region of the eye.

Alternate embodiments of the invention include analysis of motion compensation data to provide indicators pertaining to degree of control over movement. This is especially useful in measuring subtle changes in degree of control of movement.

I claim:

1. An optical coherence tomography system to measure motion control capability of a subject under test, said system including at least one depth alignment motor, wherein said depth alignment motor automatically maintains correct depth alignment of the optical coherence tomography system with respect to the retina, such that the inner limiting membrane (ILM) and retinal pigment epithelium (RPE) are substantially centered in depth scans of the optical coherence tomography system, and at least one control signal, wherein said control signal is derived from interference signals of said ILM and RPE and is operable to automatically control said alignment motor, and wherein the frequency content of said control signal provides a measure of the motion control capability of said subject under test, and wherein said system outputs said measure of the motion control capability of said subject under test.

2. The system of claim 1, wherein said system provides central macular thickness data, said data obtained as subject is performing controlled eye motion, such that the distribution curve of measurements obtained from a subject provides data eye movement control capability data.

3. The system of claim 1, wherein said system provides data pertinent to axial length alignment compensation, obtained in process of axial length measurement, such that the amount (magnitude and frequency) of alignment compensation required provides a measurement of involuntary and non-volitional eye movement.

4. The system of claim 1, said system providing a plurality of B scans along with an indicator of scan quality expressed as signal to noise ratio, wherein value of or change in signal to noise ratio provides eye movement control data.

5. The system of claim 4 wherein the optical coherence tomography system is a multiple reference optical coherence tomography system.

* * * * *